United States Patent [19]

Hirsch

[11] Patent Number: 4,526,452
[45] Date of Patent: Jul. 2, 1985

[54] METHOD AND APPARATUS FOR MEASURING CONTRAST SENSITIVITY

[75] Inventor: Joy Hirsch, New Haven, Conn.

[73] Assignee: Interzeag AG, Schlieren, Switzerland

[21] Appl. No.: 386,434

[22] Filed: Jun. 8, 1982

[51] Int. Cl.³ .............................................. A61B 3/02
[52] U.S. Cl. .................................... 351/243; 351/239
[58] Field of Search .............. 351/237, 239, 243, 211, 351/222

[56] References Cited

U.S. PATENT DOCUMENTS

| | | | |
|---|---|---|---|
| 3,969,020 | 7/1976 | Lynn et al. | 351/237 |
| 4,293,200 | 10/1981 | Dobson et al. | 351/243 |
| 4,384,768 | 5/1983 | Guzman | 351/237 |
| 4,405,920 | 9/1983 | Weisstein | 351/237 |

Primary Examiner—Rodney B. Bovernick
Attorney, Agent, or Firm—Peter K. Kontler

[57] ABSTRACT

A method is provided for testing the ability of a subject to visually perceive contrast between adjacent fields of different luminance. The subject is presented with a series of visual test patterns, each one of which includes at least two fields of differing luminance resulting in a contrast edge at the interface between the fields. The subject's ability to perceive the edge between the fields is monitored. A series of different test patterns are presented electronically to the subject on a computer-controlled screen which includes one field of constant or fixed luminance and one field of variable luminance. The luminance level of the variable field may be predetermined and varied by the computer in one protocol or controlled by the subject using a subject operated control device as an alternative protocol. In the first protocol, the computer will present on the screen a series of test patterns of different edge width and different contrast and the subject is asked to indicate whether he is able to see an edge. In the second protocol, the computer will present a series of test patterns of different edge widths and the subject is asked to adjust the luminance of the variable field to a point where the transition edge between the two fields is eliminated. In each protocol, the amount of contrast necessary for the subject to perceive an "edge" is measured. The subject's responses in either case are monitored and compared against a control.

In an alternative embodiment, the test patterns may be presented on a screen using a projection device.

21 Claims, 12 Drawing Figures

METHOD AND APPARATUS FOR MEASURING CONTRAST SENSITIVITY

BACKGROUND OF THE INVENTION

The present invention relates generally to method and apparatus for measuring the contrast sensitivity of the human eye and, more particularly, to such method and apparatus where contrast sensitivity, an indicator of visual function, is measured by determining a subject's response to luminance differences offered by a single edge, i.e., the luminance transition from a light area to a dark area.

In recent years, it has been recognized that detection of visual loss oftentimes is an early indication of eye disease. To this effect, a good and well executed test of visual function can prove to be a valuable diagnostic tool for the visual practitioner.

Perimetry is one type of visual test used for evaluating functions of the retina and the supporting neural network of the brain. In perimetry, the ability of the eye to perceive light at different retinal locations is measured. It has been found that when the retina or other portions of the visual system are impaired due to such diseases as optic neuritis, glaucoma or diabetic retinopathy, some loss of the ability of the eye to perceive light will occur. Perimetry is used to determined, as accurately as possible, those specific areas of the retina which have reduced sensitivity to small spots of light.

One example of a perimetry instrument currently available is the OCTOPUS ™ automated perimeter which is distributed by Hitron Corporation of Norwood, N.J. The OCTOPUS automated perimeter employs a computer controlled hemispherical perimeter projection system which enables the entire visual field to be examined. A similar device is described in U.S. Pat. No. 3,705,003 to Lynn et al., which utilizes a computer to control the position, size and intensity of various test stimuli which are presented on a visual display screen at predetermined locations in the subject's visual field. The subject viewing the screen responds to each stimulus using a control device to indicate whether light was perceived.

Perception of light is but one of several functions of the retina/brain system, other functions including perception of pattern, motion and color. When the retina or some other portion of the visual system is impaired due to disease, some loss of one or all of these basic functions may be expected.

Recently, there has been an emphasis on the use of pattern perception to evaluate the status of the eye. This may be done by determining the amount of contrast in a pattern necessary for the pattern to be detected by the subject. The monitoring of "contrast sensitivity" is considered a useful early diagnostic tool because an eye with pathology will, oftentimes, lose its ability to perceive patterns, i.e. contrast, before it loses its ability to perceive small spots of light. Accordingly, visual pathology may affect one's contrast sensitivity before affecting a subject's ability to perceive light small spots of light, or their visual acuity.

Pattern perception represents a complex form of vision where information from the photoreceptors of the eye is summarized by the higher centers of the brain. Accordingly, in certain eyes with early pathology, this function will show the first indication of disease. Contrast sensitivity testing thus provides a very sensitive and early indication of the onset of eye disease and may be thought of as a type of window or probe to evaluate retina-brain function and/or status.

Contrast of a pattern is determined by the difference in luminance between two adjacent light and dark areas and may be measured quantitatively by measuring the luminance of the adjacent light and dark areas. Contrast sensitivity is a measurement of the amount of contrast necessary for the eye to perceive a pattern. While in perimetry the amount of light necessary to perceive a small spot is measured, in tests of contrast sensitivity, the amount of contrast necessary to perceive a simple pattern is measured. In testing for contrast sensitivity, a strategy must be employed to vary the contrast of a particular pattern in order to determine the minimum amount of contrast necessary to detect that pattern. Contrast threshold is the smallest amount of contrast necessary to detect the pattern and may be determined using a testing strategy similar to that used by the perimetry instruments.

An example of one commercially available instrument for measuring contrast sensitivity is marketed by Optronix of Evanston, Ill.

The current commercially available instruments used to test for contrast sensitivity suffer from a number of distinct disadvantages due, in part, to the bar test patterns which they utilize. Typically, the patterns used to determine the sensitivity of a subject consist of many vertical bars of alternating light and dark stripes. The size (width) of the stripes changes for different parts of the test. However, regardless of the stripe size, what is measured is the minimum amount of contrast necessary for the subject to correctly identify that the pattern was present. This is the contrast threshold. These patterns, known as "grating patterns", are all composed of bars without sharp edges, i.e. they appear "fuzzy". More formally the bars change from a light bar to a dark bar across a space in accordance with a sinusoidal function, and are frequently referred to as sinusoidal spatial frequency gratings. The term "spatial frequency" refers to the size of the bars, i.e. a large bar is high spatial frequency. Units of size are expressed in the number of cycles (light and dark bar parts) imaged on one degree of the retina, i.e. cycles/degree.

The equipment necessary to generate the requisite bar patterns and analyze the responses thereto is extremely sophisticated. Moreover, the current tests are time-consuming. It has been found that determination of eye function by any method other than a quick screening method is particularly tiring for the patient. Using such commercially available methods, the patient may be required to return to the clinic for repeated testing sessions. This has been found to be onerous for many patients.

A further problem with the instruments commercially available to test for contrast sensitivity is that the interpretation of the contrast sensitivity function is not well understood. For example, the medical or biological significance of a shifted peak or accelerated loss of sensitivity to large bars is not known.

In the commercially available devices for measurement of contrast sensitivity, the amount of contrast necessary to detect a grating pattern is determined for many different sizes of bars (spatial frequencies). The results are displayed so that contrast or threshold (expressed in decibels or percent) is plotted against spatial frequency on the x-axis of a graph. Comparisons to the normal or expected values are determined by point to point subtractions of the subject's values. This method does not provide an overall index of how well the subject's function compared against an expected normal function. It does suggest certain possible changes in the shape of the function, i.e., that a subject has lost more sensitivity to high spatial frequencies than, for example, to low spatial frequencies. However, these types of observations can be made about how the contrast sensitivity function differs from the expected, their medical importance is not well understood. Further, in many cases it is necessary to compare the measured results to results which would normally be expected from a typical observer. Unfortunately, such normal functions vary quite markedly from each other. Accordingly, precision or accuracy is lost with the current testing procedures for contrast sensitivity because uncertainty in the comparison function is high.

OBJECTS AND SUMMARY OF THE INVENTION

Against the foregoing background, it is a primary object of the present invention to provide a method and apparatus for measuring the contrast sensitivity of a subject's eye.

It is another object of the present invention to provide such a method and apparatus which is readily able to detect early signs of eye disease.

It is still another object of the present invention to provide such a method and apparatus which can relatively simply and inexpensively present a test pattern for measuring contrast sensitivity.

It is yet still another object of the present invention to provide such a method and apparatus which can be used quickly and readily with clinical patients.

It is still yet another object of the present invention to provide such a method and apparatus wherein the measured results of contrast sensitivity are readily comparable to results from a normal eye.

It is yet another object of the present invention to provide such a method and apparatus wherein the results of the test are readily capable of being quantitatively compared against the test results of a control group.

To the accomplishments of the foregoing objects and advantages, the present invention, in brief summary, comprises a method and apparatus to determine contrast sensitivity for a subject. Rather than determining the amount of contrast necessary to detect many bar gratings of different sizes (spatial frequencies) the amount of contrast necessary to detect a single edge is determined. Thus, the test is referred to as an "Edge Test". According to the method and apparatus of the present invention, the subject is presented with a series of visual test patterns, each of which includes two adjacent fields of differing luminance defining an edge at their interface. The test patterns in the series are preselected by the computer to present a number of different edge widths. In some cases, the edge is sharp while in either case it is more gradual. For each pattern the amount of contrast necessary for the patient to detect an edge is determined by employing some strategy which increases and decreases the contrast until a threshold contrast is formed.

In a presently preferred embodiment, the test patterns are presented electronically on a visual display screen which includes a field of constant or fixed luminance and a field of variable luminance. The widths of the edges between the two adjacent fields and the luminance level of the variable field are controlled by the computer and are presented to the subject whose task is to indicate those patterns in which he or she perceives an edge between the two fields. In an alternative embodiment, the luminance level of the variable field is adjusted by the subject using an operated control device for each edge width test pattern presented by the computer on the visual display screen. For each test pattern, the subject is asked to adjust the luminance of the variable field to a point where the contrast edge between the two fields is eliminated. The ability of the subject to properly adjust the variable field is monitored and compared against a control by the computer. Regardless of the test strategy employed to determine edge threshold, the values are fit to a function where contrast as threshold (decibels) is plotted against edge width (degress on the retina of the subject). The function fit to the subject's value is compared to a similar function fit to a normal value. An index results that indicates the extent to which the subject and normal functions differ. Thus, the practitioner has a single number that indicates whether the visual system of a subject is impaired or is normal. If impaired, the number also indicates the extent of contrast sensitivity loss.

The novel features which are considered as characteristic of the invention are set forth in particular in the appended claims. The improved method and apparatus, however, both as to construction and mode of operation, together with additional features and advantages thereof, will be best understood upon perusal of the following detailed description of certain specific embodiments with reference to the accompanying drawings.

BRIEF DESCRIPTION OF THE DRAWINGS

FIGS. 3A–3C are representative samples of test patterns according to the edge test of the present invention showing two adjacent fields of different luminance connected by transitions of different widths. The diagrams on the right side illustrate the transition width between the two luminance areas specifically:

DESCRIPTION OF THE PREFERRED EMBODIMENTS

As previously discussed, contrast may be defined as the difference in luminance between two adjacent light and dark areas while sensitivity to contrast is a measurement of the amount of contrast required by a subject to see a particular test pattern. Prior art methods for measuring contrast sensitivity employed a testing procedure in which the contrast of a particular spatial frequency grating was varied to determine the minimum amount of contrast necessary by a subject to detect a pattern. Similar contrast thresholds were determined for spatial frequency gratings with bar patterns of different sizes.

Figure 1:
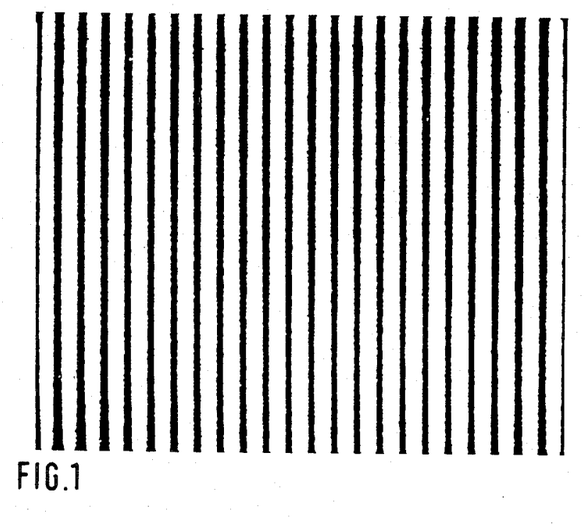
FIG. 1 is a representative sample of typical bar test patterns used in the prior art to test for contrast sensitivity.

The pattern shown in FIG. 1 is illustrative of the prior art types of the bar types of testing patterns used to measure contrast sensitivity, typically taking the form of bars of different sizes (widths).

Figure 2:
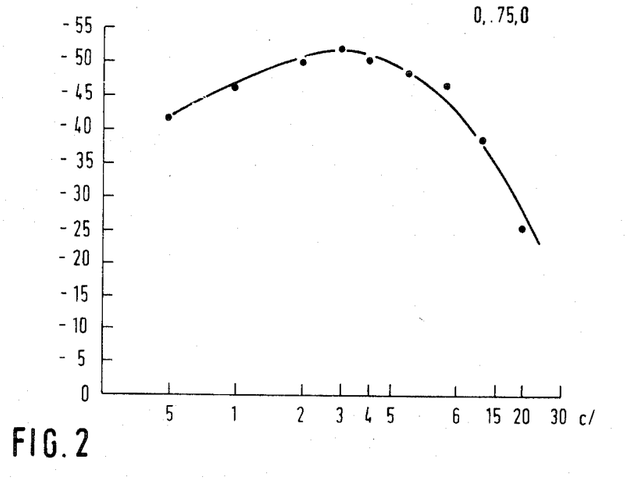
FIG. 2 is a representative prior art contrast sensitivity function plotting contrast threshold (y-axis) against test pattern bar size; (x-axis)

FIG. 2 illustrates the contrast thresholds of such test patterns, i.e., the smallest amount of contrast necessary to detect the pattern as plotted against the pattern or bar size. Contrast sensitivity functions contribute significantly to scientific explanations of how the eye-brain network codes visual information and are used clinically to assess visual functions in eyes with some pathology.

An inherent disadvantage of the prior art bar test pattern illustrated in FIG. 1 is that the equipment required to generate such a pattern and vary the contrast thereof in order to determine contrast threshold, is extremely sophisticated and is not generally commercially available. Accordingly, such techniques are not well suited for clinical environments. Moreover, the stimulus used in such procedures, called spatial frequency grating, inherently contains certain unnecessarily complicated features.

The test method of the present invention overcomes many, if not all, of the inherent disadvantages of the prior art bar test patterns in that contrast sensitivity is measured from a simple edge. The method of the present invention, referred to as an "Edge Test", relies on a determination of contrast sensitivity offered by luminance differences between two adjacent fields.

Figure 3A:
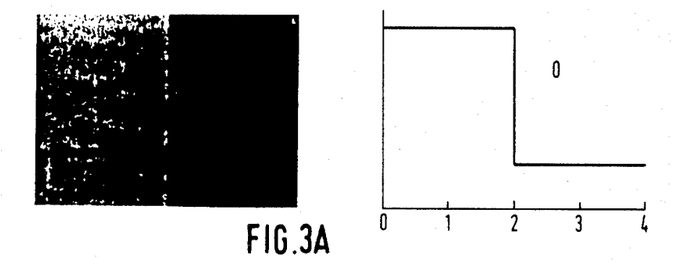
FIG. 3A is an example of a contrast sensitivity test pattern with the bright side on the left and the dark side on the right. The transition between the two patterns is sharp, i.e. sudden as in a step function shown on the right.
Figure 3B:
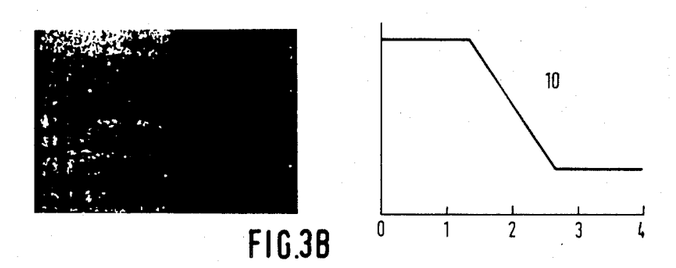
FIG. 3B is an actual contrast sensitivity test pattern according to the test of the present invention showing a more gradual transition edge between two adjacent fields of different luminance which is illustrated by the drawing on the right.
Figure 3C:
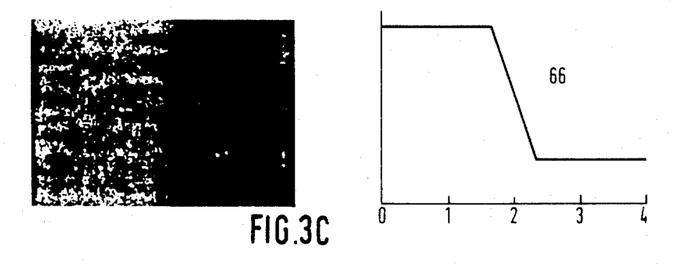
FIG. 3C is a contrast sensitivity test pattern according to the test of the present invention showing a particularly gradual transition edge between the two adjacent fields of different luminance which is illustrated by the drawing at the right.

The luminance profiles at the right in FIGS. 3A, 3B and 3C diagramatically illustrate typical types of edge test patterns. The patterns vary with respect to the size of the transition from one luminance field to the other. The left hand pictures depict actual patterns and ar photographs taken from the accompanying screen monitor displays illustrating the edge test patterns as they would appear to the subject.

In FIG. 3A, where the transition size is 0°, a sharp transition is provided between the adjacent fields. In FIG. 3B, there is a more gradual transition from the light field to the dark field as evidenced by its transition size of 0.66°. In FIG. 3C there is a still more gradual transition between the light and dark fields as evidenced by its transition size of 1.0°. It will further be appreciated that by varying the luminance levels for the adjacent fields for each test pattern, a myriad of different test combinations may be presented to the subject.

It will be appreciated that the test pattern of FIG. 3A offers a well defined edge stimulus i.e., the luminance transition from light to dark field is sharp, thus providing an optimal stimulus for the eye.

The transition edge presented in the test pattern of FIG. 3B is somewhat more difficult to perceive by the subject because of its increased transition size, i.e., 0.66°. The test pattern of FIG. 3C is still more difficult to perceive because the transition edge between the adjacent luminance fields is even larger, i.e., a transition size of 1.0°.

Figure 4:
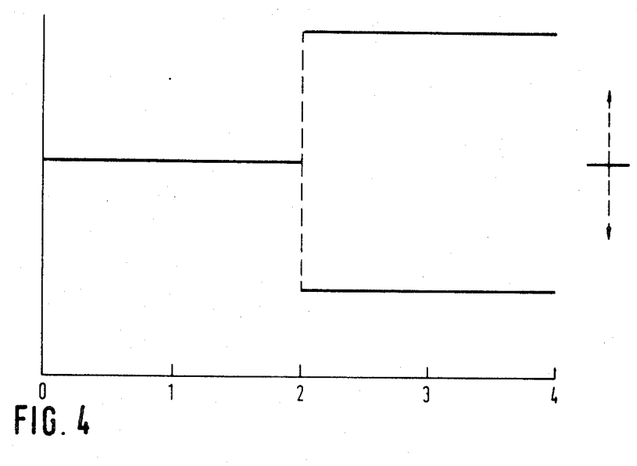
FIG. 4 diagramatically illustrates the testing task of the edge test method of the present invention.

FIG. 4 illustrates the testing strategy of the edge test method of the present invention. The task of the subject, which is the same for all test patterns presented, is to indicate whether or not an edge is perceived. To this effect, the test is similar to perimetry tests wherein a subject must indicate whether or not light is perceived.

The test strategy of the present invention may vary. In a preferred embodiment, the test patterns are presented to the subject electronically on a visual display monitor or screen. The screen is divided into two fields, one is kept at a constant or fixed luminance level while the luminance of the other field may be varied above and below the luminous level of the constant field. This is shown, for example, in FIG. 4 where one half of the screen width, identified as a "Fixed Side", is maintained at a constant luminance level while the luminance level of the other field may be adjusted above and below level of the fixed side.

As will be described in greater detail, the edge test of the present invention may be administered in a variety of different ways. For example, one method contemplates the subject being presented with a series of random test patterns wherein the edge width and luminance level of the variable field are controlled by the computer. The subject would indicate whether he or she was able to perceive an edge following each presentation of a pattern. In another embodiment, the computer selects a particular test pattern and the subject is instructed to adjust the luminance level of the variable field using a control until the edge either disappears or reappears.

Figure 5:
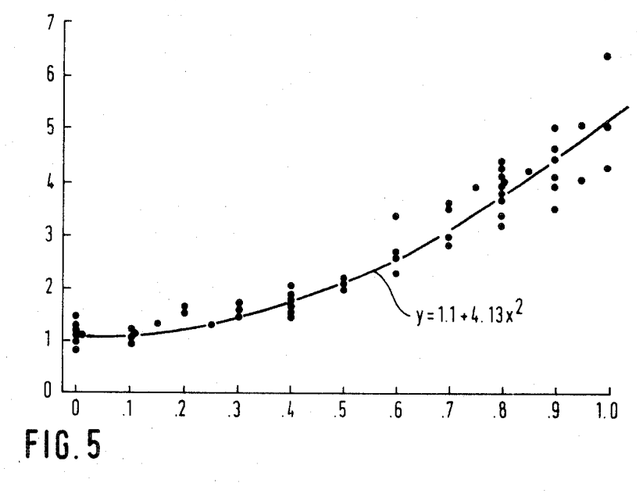
FIG. 5 is a graph plotting contrast sensitivity test performance using the edge test of the present invention against the width or sharpness of the edge for normal observers.

The test method of the present invention contemplates that a group of normal subjects would be tested and their responses used as a control against which all subjects will be compared. FIG. 5 graphically demonstrates the test performance of a control group of well studied normal observers, plotting their respective test performances against edge width. For illustrative purpose, the edge width of 0° corresponds to the test pattern shown in FIG. 3A; the edge width of 0.66° corresponds to the test pattern of FIG. 3B; and the edge width of 1.0° corresponds to the yet more subtle test pattern shown in FIG. 3C.

As can, of course, be appreciated, as the edge width increases, it becomes more difficult for the observer to perceive. This relationship has been quantified by the following formula:

$$y = 1.1 + 4.13x + \text{error}$$

wherein x represents the transition size of the edge in degrees of visual angle subtended on the eye of the subject and y represents a measure of the amount of contrast necessary to perceive the edge. This relationship was determined from data obtained from normal subjects. This relationship has been found to be relatively constant for all normal observers and thus, unlike the traditional or familiar contrast sensitivity test functions of the prior art, the edge test function of the present invention is more stable across different observers.

The procedure by which the edge test is conducted may vary. What is important, however, is that the results of the test must be capable of being automatically monitored and compared against the control group results.

In a preferred embodiment, the test patterns are presented to the subject electronically by way of a stimulus display monitor or screen. One side or field of the screen is pre-set at a constant luminance level while the luminance level on the other field is variable as shown and earlier described with respect to FIG. 4. The transition edge is created by the luminance differences between the adjacent fields. The computer randomly selects and presents a number of different test patterns on the screen. These patterns will include transition edges of different widths as well as of different contrasts for each edge width pattern.

Figure 6:
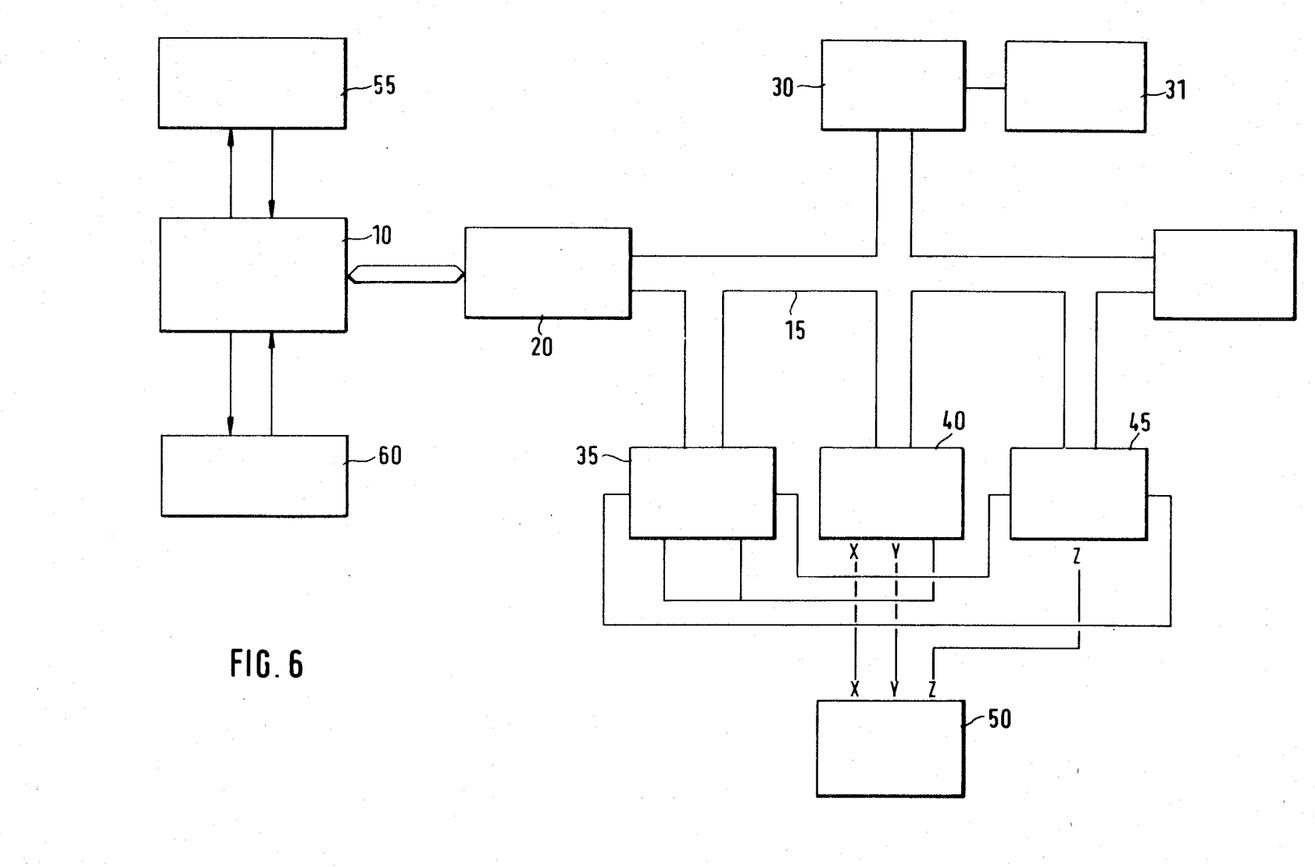
FIG. 6 is a schematic diagram of a preferred configuration of generating edge test patterns and effecting the test method of the present invention.

In a presently preferred embodiment, a computer controlled system is used. The system, which consists of a programmable controller, function modules and software, is designed to operate with a high degree of automation to enhance both the efficiency and the objectivity of data collection. This system is schematically shown in FIG. 6.

Control of the system is carried out by a computer 10 which requires modest size and speed, some mass storage, a real time clock and real time operating system and a means of communicating with the operators.

The edge test is performed by running a program on the computer 10 which communicates with both the operator and observer, oversees the operation of the laboratory equipment and gathers the desired data for later or immediate analysis.

A module bus 15 links the various modules together and provides a communication path to the computer 10. Two modules are necessary for operation of the bus. The first is the bus controller 20 which controls operation of the module bus 15 to perform an operation initiated by the system computer 10 through its own interface.

Hardware functions are carried out by function modules which operate semi-automatically. Function modules which may be used include a response module 30, a memory module 35, a scan generator 40, and an analog function module 45.

The response module 30 includes a response keyboard control 31. A response is made by the observer on the keyboard 31 following each trial which is recorded by the computer 10.

The memory module 35, scan generator module 40, and analog function module 45 are all adjusted to perform the functions of stimulus generation and their inter-relationship is shown schematically in FIG. 6.

Stimulus edge transition patterns are computed by the controller 20 and stored in the memory module 35. Test patterns are digitally generated, thus providing considerable flexibility in the kind of test patterns which can be generated.

Stimulus edge test patterns are electronically generated and displayed on a high intensity, high resolution display monitor 50. The laboratory software consists of detailed algorithms to be implemented by the controller 20 and function modules. The software is capable of interacting with the operator conducting the test to set parameter options for the desired test and then supervises the course of the session. The software issues commands necessary to the function modules, performs all necessary communication with the operator, and gathers and analyzes the resulting data.

Each different test is controlled by its own program. Session specific options are entered by a system of question and answers entered by the operator on the teletype 60. After the stimulus parameters are entered, the course of a test session proceeds completely under software control.

The computer 10 selects and displays, in random fashion, a series of test patterns each of a predetermined edge width and contrast between the two fields. In one preferred embodiment, the computer 10 will preselect and randomly present on the screen 50 various test patterns of differing edge widths and differing contrasts between the two fields. Contrast differences are created by varying the luminance of the variable field of the screen 50. For each particular edge width test pattern, a number of different luminance levels will be utilized in order to determine the subjects's contrast threshold. In this embodiment, the subject is asked to indicate on the keyboard control 31 whether he is able to perceive an edge following each trial. The subject's responses are recorded and analyzed by the computer 10.

In a second embodiment, the computer 10 will still preselect the edge width patterns presented on the screen 50 to the subject, however, the subject, by use of a control at the keyboard 31, is asked to adjust the luminance level of the variable field either higher or lower until the transition edge disappears due to an equaling of the luminance levels between both fields. The subject's response is then stored in the computer 10 and the next test pattern is automatically presented.

In each of these embodiments, a plurality of test patterns are presented to each subject in each session.

Figure 7:
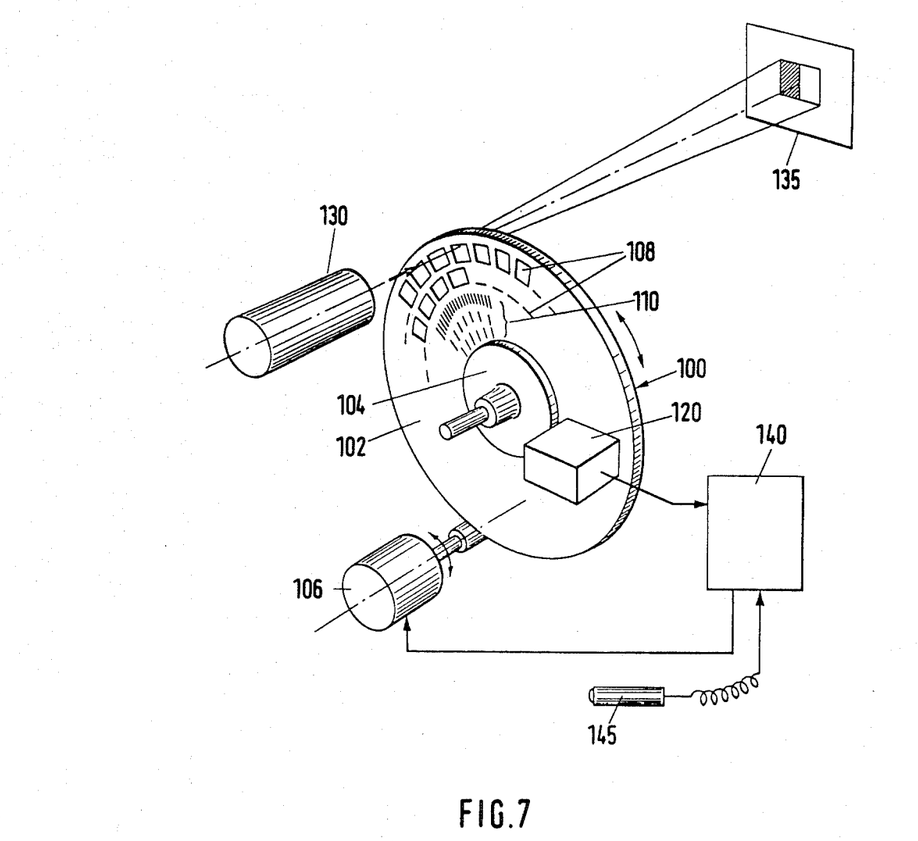
FIG. 7 schematically illustrates an alternative embodiment for mechanically generating test patterns of the present invention.

The test models which are necessary for the practice of the novel "edge test" may also be presented mechanically i.e. with a projection device. In order that the correct diapositive be rapidly selected and placed into the projection position, the optomechanical management may be constructed as shown in FIG. 7. A mechanical projection system 100 is provided which includes a disc or wheel 102 having around its periphery one or more rows of slides, each having different test patterns. Each slide is coded with a particular identification code 110. Disc 102 is adapted to pivot around hub 104 and is powered by motor 106. A code reader 120 interconnected to a computer 140 is provided for turning disc 102 such that appropriate slide 108 is properly aligned so that the test pattern contained thereon may be projected onto screen 135 by projector lamp 130. A response button 145 may be used by the subject to indicate when an appropriate response is required. It will of course be appreciated that one or more projector lamps could be employed to vary the intensity of light through slides 108 as well as other modifications without departing from the spirit and scope of the present invention.

Figure 8:
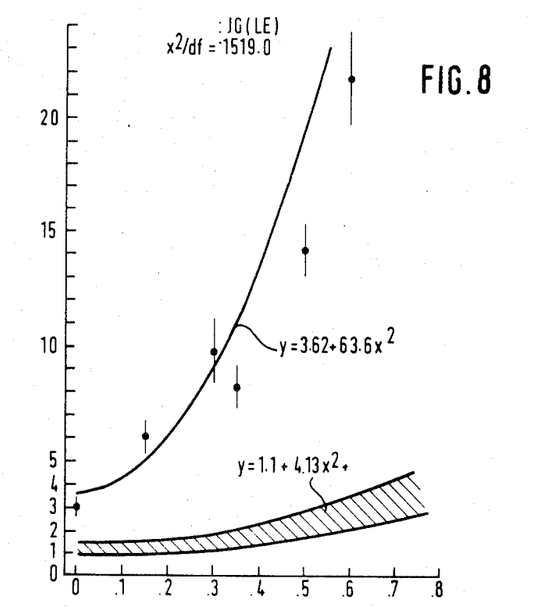
FIGS. 8, 9 and 10 illustrate sample contrast sensitivity test performances of typical subjects tested with the test method of the present invention.
Figure 9:
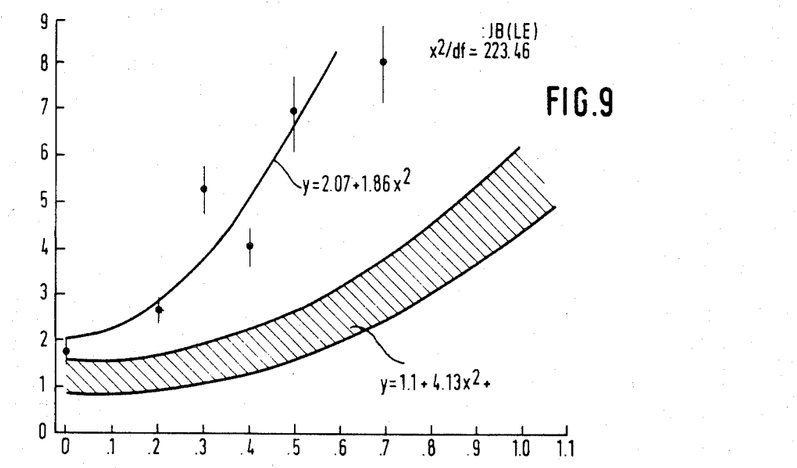
Figure 10:
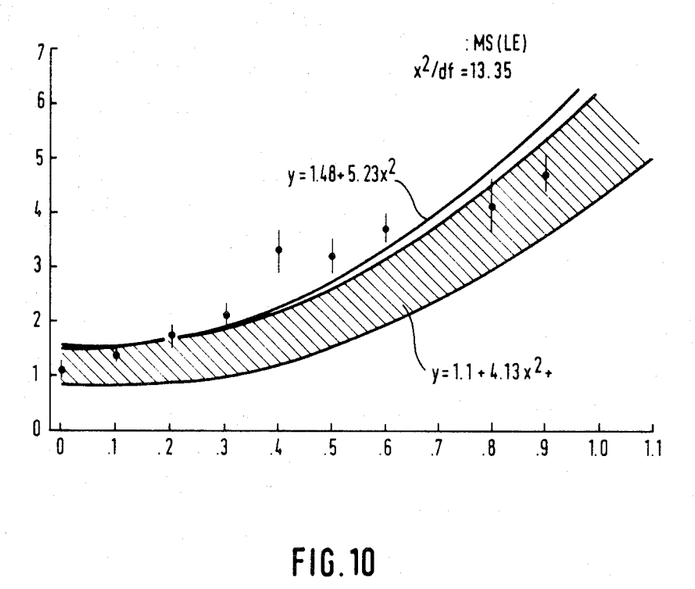

FIGS. 8-10 are illustrative of the results of actual edge tests conducted on subjects with certain eye pathologies. The three patients tested were insulin controlled, childhood onset diabetics with normal visual acuity, i.e., 20/20 or better in each eye.

FIG. 8 illustrates the results of an edge test conducted on the left eye of one of the subjects. The expected range for the control subjects as a reference is shown in the shaded area of FIG. 8. The data demonstrate that this subject required a greater contrast to perceive an edge at all edge widths than the control subjects. Accordingly, sensitivity to contrast for this subject was severely reduced.

An important feature of the method of the present invention is its ability to quantify the specific magnitude of difference between the contrast sensitivity of the tested subject and the norm. A reference number has been established to compare the results of each function by determining the chi squared value per degree of freedom.

It will, of course, be appreciated that the above method of deriving a reference number is but one possible algorithm which may be used to quantify the test results and other algorithms may also be employed without departing from the spirit and scope of the present invention.

The advantage offered by providing such a reference number is that it is based on a function rather than on a single point estimate and provides the visual practitioner with a specific reference number for use in subsequent diagnosis. The reference number for normal controlled observers would be approximately $5 \pm 3$. The subject tested in FIG. 8 had a reference number of 1519.0 which indicates a severe loss of contrast sensitivity despite the fact that his or her visual acuity was normal.

The results of the edge tests of FIGS. 9 and 10 are illustrative of less severe retinopathy conditions resulting in reference numbers of 223.46 for the subject of FIG. 9 and 13.35 for the subject of FIG. 10. The subject tested in FIG. 9 would appear to have a preretinopathy condition while the test results for the subject tested in FIG. 10 would be suspicious, The following examples serve to further illustrate the efficacy of the edge test method of the present invention when used as a diagnostic tool on subjects complaining of visual loss but with no known eye pathology.

EXAMPLE 1

The edge test of the method of the present invention was conducted on a subject complaining of visual loss in the left eye. The visual acuity in the left eye was 20/40 and the perimetry test results were normal.

The edge tests results were as follows: right eye 15.61, left eye 22.63. These test results indicate a discernable difference between the two eyes with both values demonstrating a moderate loss of contrast sensitivity. The results suggest an early pathology of the left eye and confirm the subject's complaint of visual loss.

EXAMPLE 2

A subject was tested using the edge test after having complained of inferior temporal quadrant cloud in the left eye. The visual acuity results were 20/15 (normal) and the perimetry test results were normal. The edge test results were as follows: right eye 3.12, left eye 19.94.

These edge test results show a difference between the two eyes. While the edge test results for the right eye were within normal limits, the results for the left eye demonstrated a moderate loss of contrast sensitivity. The edge test confirmed and quantified the subject's complaint. Further follow-up testing proceeded on the basis of these test results.

EXAMPLE 3

A subject was tested using the edge test after complaining of a sudden onset of dimness in the left eye for approximately 4 weeks. The visual acuity was normal in both eyes and normal perimetry test results were obtained. The edge test results were as follows: left eye 570.5; right eye 138.7.

The results of the edge test confirmed marked loss of contrast sensitivity in both eyes. Th visual loss was most severe for the left eye and was consistent with the subject's complaint of dimness in that eye.

EXAMPLE 4

A subject was tested using the edge test after a preliminary diagnosis of disease with reduced visual acuity in the left eye. Visual acuity in the left eye was measured as 20/50. No perimetry tests were run. The edge test results were as follows: left eye 1847, right eye 34. These values indicated substantial loss of sensitivity to the edges in the left eye and the right eye examination was suggestive of minimal loss. The edge test results confirmed and quantified the subject's complaint.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

What is claimed is:

1. A method of testing the ability of a subject to visually perceive a transition edge between adjacent fields of different luminance, said method comprising the steps of:
   establishing a plurality of visual test patterns each of which includes only two adjacent fields of different luminance defining a single transition edge at the interface between the adjacent fields, the adjacent fields defining different transition edges from test pattern to test pattern;
   presenting to the subject a serious of successive visual test patterns of said plurality of visual test patterns; and
   monitoring the ability of the subject to perceive the single transition edge between the fields for each of said series of successive patterns.

2. The method of as defined in claim 1 wherein the width of the single transition edge varies from one test pattern to another.

3. The method as defined in claim 2 wherein the test patterns presented are preselected by a computer and wherein the patterns are electronically presented to the subject on a screen.

4. The method as defined in claim 3 wherein the luminance of one field is constant and the luminance of the other field is variable.

5. The method as defined in claim 4 wherein the luminance of the variable field is preselected by the computer.

6. The method as defined in claim 4 wherein the luminance of the variable field is controlled by the subject using a control device.

7. The method as defined in claim 5 wherein the transition edge width and the luminance difference between the fields for each test pattern are predetermined by the computer.

8. The method as defined in claim 6 wherein the transition edge width for each test pattern and the initial luminance difference between the fields are predetermined by the computer and wherein the ability of the subject to perceive is determined by monitoring his ability to adjust the luminance of the variable field until the transition edge is no longer visible.

9. The method as defined in claim 1 further comprising the step of comparing the results of the test against a control and assigning a reference number for each test wherein the reference number indicates the extent of visual loss.

10. The method as defined in claim 1 wherein the test patterns are projected onto a screen by a projection device.

11. A method of testing the ability of a subject to visually perceive a transition edge between adjacent fields of different luminance, said method comprising the steps of:
establishing a plurality of visual test patterns each of which includes only two adjacent fields of different luminance defining a single transition edge at the interface between the adjacent fields, the difference of luminance levels between the two fields being varied for each test pattern;
presenting to the subject on a screen a series of successive visual test patterns of said plurality of visual test patterns; and
monitoring the ability of the subject to perceive the single transition edge of each test pattern of said series of successive visual test patterns.

12. The method as defined in claim 11 further including the step of comparing the ability of the subject to perceive against the ability of a control group to perceive.

13. A method of testing the ability of a subject to visually perceive a transition edge between adjacent fields of different luminance, said method comprising the steps of:
establishing a plurality of visual test patterns each of which includes only two adjacent fields of different luminance defining a single transition edge at the interface between the adjacent fields, one of said fields in each visual test pattern having a constant luminance level and the other of said fields in each visual test pattern having a variable luminance level to be adjusted by the subject;
presenting to the subject on a screen a series of successive visual test patterns of said plurality of visual test patterns; and
monitoring the ability of the subject to adjust the luminance level of the variable field of said series of successive visual test patterns until the single transition edge is not visible.

14. The method as defined in claim 13 wherein said monitoring step includes presenting the subject with the opportunity to provide "yes" and "no" responses to each of said series of successive visual test patterns.

15. Apparatus for testing the ability of a subject to visually perceive a transition edge between adjacent fields of different luminance, said apparatus comprising:
means for establishing a plurality of visual test patterns each of which includes only two adjacent fields of different luminance defining a single transition edge at the interface between the adjacent fields, the adjacent fields defining different transition edges from test pattern to test pattern;
means for presenting a series of successive test patterns of said plurality of visual test patterns for viewing by a subject; and
means for determining the ability of the subject to perceive said transition edge for each of said series of successive visual test patterns.

16. The apparatus of claim 15 wherein said means for presenting comprises a video monitor on which said patterns are presented.

17. The apparatus as defined in claim 16 wherein the luminance level of one of said fields is constant and the luminance level of said other field is variable.

18. The apparatus of claim 15 wherein said means for presenting comprises projection means.

19. The apparatus of claim 15 further comprising means for preselecting said series of test patterns.

20. The apparatus of claim 15 further comprising means for controlling the width of the transition edge of each pattern.

21. The apparatus of claim 17 wherein said means for determining comprises control means whereby the subject may adjust the luminance level of the variable field.

* * * * *